United States Patent [19]

Dolhyj et al.

[11] Patent Number: 4,710,484

[45] Date of Patent: Dec. 1, 1987

[54] METHOD FOR PREPARING A SUPPORTED MIXED-METAL OXIDE OXIDATION CATALYST

[75] Inventors: Serge R. Dolhyj, Parma; Wilfrid G. Shaw, Lyndhurst; Marc A. Pepera, Northfield Center, all of Ohio

[73] Assignee: The Standard Oil Company, Cleveland, Ohio

[21] Appl. No.: 392,199

[22] Filed: Jun. 25, 1982

[51] Int. Cl.[4] ...................... B01J 27/14; B01J 27/198; B01J 27/188; B01J 27/19

[52] U.S. Cl. .................................... 502/208; 502/209; 502/210; 502/211; 502/212; 502/302; 502/304; 502/321; 502/322; 549/257; 549/258; 549/259

[58] Field of Search ........... 252/435, 437, 458, 455 R, 252/462, 465

[56] References Cited

U.S. PATENT DOCUMENTS

| | | | |
|---|---|---|---|
| 3,642,930 | 2/1972 | Grasselli et al. | 252/437 X |
| 3,864,280 | 2/1975 | Schneider | 252/435 |
| 3,959,182 | 5/1976 | Izawa et al. | 252/467 |
| 3,985,775 | 10/1976 | Harrison | 252/437 X |
| 4,017,423 | 4/1977 | White et al. | 252/435 X |
| 4,042,533 | 8/1977 | Shaw et al. | 252/437 |
| 4,147,661 | 4/1979 | Higgins et al. | 252/435 |
| 4,158,671 | 6/1979 | Barone | 252/435 X |
| 4,222,945 | 9/1980 | Higgins | 502/209 X |
| 4,276,222 | 6/1981 | Mount et al. | 252/437 X |
| 4,301,030 | 11/1981 | Shaw et al. | 252/435 |
| 4,301,031 | 11/1981 | Shaw et al. | 252/435 |
| 4,333,853 | 6/1982 | Milberger et al. | 252/437 X |
| 4,364,844 | 12/1982 | Umenura et al. | 252/435 |
| 4,374,757 | 2/1983 | Khoobiar | 252/435 X |
| 4,377,501 | 3/1983 | Khoobiar | 252/435 X |
| 4,396,535 | 8/1983 | Burner et al. | 502/208 |
| 4,444,906 | 4/1984 | Callahan et al. | 502/209 X |

OTHER PUBLICATIONS

U.S. application Ser. No. 222,821, filed 1-5-81, by Grasselli et al. entitled "Process".

U.S. application Ser. No. 235,353, filed 2-17-81, by Callahan et al. entitled "Composite Catalyst for the Single Stage Conversion of Propylene to Acrylic Acid".

*Primary Examiner*—Andrew Metz
*Assistant Examiner*—William G. Wright
*Attorney, Agent, or Firm*—M. F. Esposito; J. E. Miller; L. W. Evans

[57] ABSTRACT

Improved supported, mixed-metal oxide oxidation catalysts are prepared by conditioning a devolatilized catalyst precursor with an alcohol prior to calacining the precursor to a finished catalyst. For example, a promoted bismuth phosphomolybdate oxidation catalyst useful for converting propylene to acrolein demonstrates enhanced performance characteristics when the devolatilized catalyst precursor is subjected to boiling ethanol prior to calcining it to a finished catalyst.

10 Claims, No Drawings

METHOD FOR PREPARING A SUPPORTED MIXED-METAL OXIDE OXIDATION CATALYST

BACKGROUND OF THE INVENTION

1. Field of the Invention

This invention relates to catalysis. In one aspect, the invention relates to supported, mixed-metal oxide oxidation catalysts while in another aspect, the invention relates to a method for preparing these catalysts. In yet another aspect, the invention relates to the conditioning of a supported, mixed-metal oxide catalyst precursor with an alcohol.

2. Description of the Prior Art

Supported, mixed-metal oxide catalysts are well known in the art as well as numerous methods for their preparation. These catalysts typically contain two or more metals, such as molybdenum and bismuth, and frequently contain non-metallic components, such as phosphorus. A typical preparation for these catalysts commences with contacting a preformed support with an aqueous solution or dispersion of the catalyst components, drying the resulting impregnated support, reducing the volatile (nitrates, carbonates, etc.) content of the impregnated support, and then calcining the volatile-reduced, impregnated support to a finished catalyst. Many variations on this scheme exist including using aqueous and non-aqueous media for impregnating the support, variations on drying and reducing the volatile content, and different techniques of calcination. While all of these processes produce finished catalysts suitable for their intended purpose of promoting oxidation reactions, some work better than others and none are entirely satisfactory. Consequently, there exists a continuing search for new and better methods for preparing these kinds of catalysts.

SUMMARY OF THE INVENTION

According to this invention, the method of preparing a supported, mixed-metal oxide oxidation catalyst by first forming a catalyst precursor with a volatile content from a support and the mixed-metal components, and subsequently reducing the volatile content of the precursor and then calcining the precursor to a finished catalyst is improved by conditioning the catalyst precursor with at least one alcohol subsequent to reducing the volatile content of the precursor but prior to calcining it to a finished catalyst. Oxidation catalysts prepared by this method generally display improved activity and selectivity in their intended reactions as compared to catalysts prepared without undergoing the alcohol conditioning step.

DETAILED DESCRIPTION OF THE INVENTION

Catalyst Composition

This invention can be used to manufacture finished catalyst particles of widely different composition. These catalysts are mixed-metal oxides, i.e. oxide compositions containing two or more metals, that can also contain nonmetal components. This invention is particularly useful for preparing catalysts containing molybdenum in combination with at least one metal element selected from Group IA, IIA, IIIB, VB, VIB (excluding Mo), VIIB, VIII, IB, IIB, VA, VIA and the rare earth elements of the Periodic Table as published by E. H. Sargent and Company (1964), especially catalysts having the composition of the empirical formula $$Mo_{12}P_{0\text{-}3}M_{0.01\text{-}10}O_x \qquad (1)$$

where M is at least one of potassium, rubidium, cesium, barium, zinc, cadmium, titanium, calcium, magnesium, tungsten manganese, tantalum, zirconium, cerium, nickel, cobalt, chromium, iron, thallium, bismuth, copper, vanadium, niobium, a rare earth metal, arsenic and antimony; and x is a number that satisfies the valance requirements of the other elements present. Usually M is a combination of at least two and preferably at least three metal components (preferably with bismuth as one of the components) and catalysts where M includes an alkali metal, bismuth and at least one of iron, cobalt and nickel are well suited for preparation by this invention. The method of this invention is also particularly useful for preparing catalysts having the compositions of those catatysts described in U.S. Pat. Nos. 3,642,930; 4,017,423; 4,042,533; 4,301,030 and 4,301,031. The disclosures of these patents are here incorporated by reference.

The catalysts prepared by this invention are supported catalysts and any suitable support can be used. These supports can be either shaped (preformed), e.g. a tablet, sphere or microsphere, or shapeless, e.g. a sol or fine powder, and in either case can be composed of such diverse materials as silica, alumina, titania, zirconia, silicon carbide, boron, carbon, various phosphates, etc. The amount of support used and the method by which the catalyst components are admixed with or loaded onto the support can vary to convenience and catalyst purpose.

Method Procedure

The first step of this invention is the preparation of a catalyst precursor. This material is a combination of the various catalyst components in combination with a support. The precursor can be prepared in any one of a number of different methods but where the support is preformed, a typical method of preparation is to mix the appropriate catalyst components in the proper portions in an aqueous mixture and then contact this mixture with the support to load (impregnate or coat) the latter with the former. The wet support is then dried, with or without a reducing agent, and subsequently devolatilized. In another typical method, the support material is sequentially contacted with individual aqueous solutions of the various catalyst components rather than with just one aqueous solution of all the catalyst components. In yet another method of preparation, the various catalyst components are dissolved or dispersed in nonaqueous media prior to being contacted with the support material. If a sequential loading method is used, the catalyst components can be added in any order but, depending upon the catalyst to be prepared, certain orders may be preferred to other orders or simply a random order. For example, in preparing a catalyst precursor of a promoted phosphomolybdic oxide catalyst, the metal volatiles are typically formulated into an aqueous solution or slurry and contacted with the support material prior to impregnating the material with the phosphorus and molybdenum components.

In yet another variation on these methods, the aqueous solutions of the catalyst components can be pH adjusted to some predetermined level and then aged prior to loading. For example, when preparing a promoted phosphomolydic oxide catalyst, the aqueous solutions used to prepare the catalyst precursor are typically pH adjusted, if necessary, to an acid range, e.g. 3–5.

Where the support is shapeless, a typical method of forming a catalyst precursor is to mix the support (usually a sol) with an aqueous or nonaqueous mixture of the catalyst components to form a slurry and then spray dry the slurry. The resulting dry product is usually in the form of a fine powder that can be subjected to further treatment, e.g. devolitalization, conditioning, etc., prior to being used as such or being shaped (e.g. tabletted). Once the catalyst precursor has been formed, it is usually subjected to a devolatilization procedure, i.e. reduction or removal of the volatile content. By the term "volatile" is meant a substance of the catalyst precursor that will vaporize, decompose and/or oxidize when subjected to sufficient heat for sufficient time and thus be removed from the precursor. Representative volatiles include nitrates, halides, carbonates, acetates, and the like. Typically these substances are introduced into the precursor as the counter ion to one or more of the metal components in the catalyst, e.g. potassium nitrate, copper acetate, etc. The various nitrates ($NO_x$) are the preferred volatiles and reduction or removal of these volatiles is commonly referred as denitrification.

The temperature and time required to reduce the volatile content of the precursor will vary with, among other factors, the nature of the volatile but where the volatile is a nitrate, a temperature range of 150° to about 300° C. and a time range of 0.1 to 24 hours is typical. Of course, the degree of devolatilization will also vary with such factors as the nature of the volatile, the nature of the support, the temperature to which the precursor is subjected and the length of time of this exposure, etc., but preferably the precursor is devolatilized such that a substantial amount (greater than about 50 weight percent) of the initial volatile content is removed. Perferably, greater than 75 weight percent of the initial volatile content is removed.

After the precursor has been devolatilized, it is then subjected to conditioning with an alcohol. While the nature of this conditioning is not fully understood, the net effect of this treatment is to enhance the performance of the catalyst in its intended use. The alcohols here used can be selected from a wide variety of materials but it is generally at least one of the $C_1$–$C_8$ aliphatic alcohols with methanol, ethanol, n-propanol, isopropanol, t-butyl alcohol, and octanol, being exemplary. Although these materials are usually used alone, they can be used in combination with one another or in combination with other materials, such as aldehydes, carboxylic acids, ketones, halogenated hydrocarbons (e.g. chloroform, perchloroethylene, etc.) and hydrocarbons (e.g. cyclohexene, cyclohexane, benzene, toluene, kerosene, etc.).

The manner in which the devolatilized precursor is conditioned can also vary. The conditioning can be effected by contacting the precursor at atmospheric pressure with boiling alcohol for at least about 5 minutes and preferably for at least about 60 minutes. Other means for effecting the conditioning of the support is to contact it with gaseous alcohol at an elevated temperature.

Once the devolatilized catalyst precursor is conditioned, it is finished or activated by calcination. Here too, the conditions of this step will vary with the catalyst composition and its intended use, but generally they involve exposing the precursor to oxygen or air at an elevated temperature (usually greater than the temperature at which the finished catalyst will be used) for some predetermined period of time. This finishing or calcination step can either proceed use of the catalyst or be done in situ.

The method of this invention is more fully described by the following examples. Unless indicated to the contrary, all parts and percentages are by weight.

SPECIFIC EMBODIMENTS

Fluid-bed Catalysts

The catalysts of Examples A.1-.3, 1.1-.4 and 2.1-.2 were prepared by impregnating a microspheroidal silica with an aqueous solution of ammonium heptamolybdate (AHM), drying and then calcining it at 750° C. to achieve a 10 weight percent Mo $O_3$ on the silica. This silica was subsequently treated by a 2-step impregnation using aqueous solutions of (1) AHM and (2) mixed-metal nitrates (MMN) of potassium, nickel, cobalt, iron, bismuth and phosphoric acid. After first impregnating the support with AHM, the support was dried prior to impregnating it with MMN. The catalysts were then devolatilized by subjecting them to 325° C. for 4.5 hours. For those catalysts that were prepared in accordance with this invention, they were subjected to boiling ethanol (methanol in Examples 2.1 and 2.2) at atmospheric pressure for 5 hours and then allowed to dry. Both the conditioned and unconditioned catalysts were then finished by calcining for about two hours at 550° C. The microspheroidal silicas were supplied by Akzo Chemie.

The chemical composition of the catalysts prepared above are known to be effective for the oxidation of propylene to acrolein. The catalysts prepared above were compared to one another by using them as catalysts in this reaction. The reaction was conducted in 40 cc fluid-bed reactor heated with a saltbath. Liquid products were analyzed using a Hewlett-Packard Model 5710 gas chromatograph equipped with 10 percent SP1200 10-foot by ⅛ inch glass column (for acrolein and acetaldehyde) and 15 percent polyester FF 6 foot by ⅛ inch glass column (for acetic acid). Total acid determination was made by titration. The contact time was approximately 6–7 seconds and a propylene/air//nitrogen feed of 1/8/3 was used. The reaction was conducted at a temperature of 320°–350° C. The results of this comparison are reported in Table I.

TABLE I

COMPARISON OF ALCOHOL-CONDITIONED AND UNCONDITIONED FLUID-BED CATALYSTS IN THE OXIDATION OF PROPYLENE TO ACROLEIN AND ACRYLIC ACID

| Ex. | Alcohol Conditioned | Temperature (°C.) | Propylene Conversion (mole %) | % Corrected PPC* to Acrolein | Acrylic Acid | Total |
|---|---|---|---|---|---|---|
| A.1 | No | 350 | 91.5 | 77.3 | 7.3 | 84.6 |
| A.2 | No | 340 | 93.9 | 77.3 | 6.1 | 83.4 |
| A.3 | No | 330 | 84.4 | 72.7 | 4.3 | 77.0 |

TABLE I-continued

COMPARISON OF ALCOHOL-CONDITIONED AND UNCONDITIONED FLUID-BED CATALYSTS IN THE OXIDATION OF PROPYLENE TO ACROLEIN AND ACRYLIC ACID

| Ex. | Alcohol Conditioned | Temperature (°C.) | Propylene Conversion (mole %) | % Corrected PPC* to Acrolein | Acrylic Acid | Total |
|---|---|---|---|---|---|---|
| 1.1 | Yes | 330 | 97.6 | 79.6 | 8.1 | 87.7 |
| 1.2 | Yes | 335 | 95.5 | 76.7 | 8.6 | 85.3 |
| 1.3 | Yes | 330 | 95.6 | 78.2 | 7.5 | 85.7 |
| 1.4 | Yes | 335 | 97.0 | 78.4 | 8.4 | 86.8 |
| 2.1 | Yes** | 335 | 95.6 | 78.3 | 7.9 | 86.2 |
| 2.2 | Yes** | 340 | 96.6 | 78.0 | 8.4 | 86.4 |

$$*\% \text{ Corrected PPC} = \frac{\% \text{ PPC}}{\text{Carbon Balance}} \times 100$$

**Methanol

The above catalyst compositions were of the same empirical formula but the control catalyst (Ex A.1-.3) was not subjected to the alcohol conditioning. Each catalyst was tested twice with Examples 1.3 and 1.4 being a repeat of Examples 1.1 and 1.2, respectively. As the data shows, the alcohol conditioned catalysts produced a higher per pass conversion of acrolein and acrylic acid than the unconditioned catalyst at a lower temperature.

Fixed-bed Catalysts

The catalysts of Examples B.1-.2 and 3.1-.2 were of the same chemical composition as the catalysts of Examples A.1-.3, etc., and were prepared by mixing an Aerosil(®) silica (by Dequssa, Inc.) and aqueous mixtures of the catalyst components to form a slurry, spray drying the slurry to form a catalyst precursor fine powder, devolatilizing the powder, and forming the powder into tablets (using graphite (1.5 weight percent) as a binder. A portion of the tablets (70 g) were placed in a one liter round bottom flask to which was added absolute ethanol (200 ml). The contents of the flask were then sufficiently heated by a waterbath to cause the ethanol to boil and this condition was maintained for approximately 5 hours after which the contents of the flask were allowed to cool. The tablets were removed by filtration, washed with three 40 ml portions of absolute ethanol and allowed to partially dry in air. The tablets were then placed in an oven to dry overnight at approximately 1000° C. Subsequently, the tablets were calcined for 5 hours at 560° C. in the presence of air. These catalysts were used in Examples 3.1 and 3.2. The catalyst tablets used in Examples B.1 and B.2 were calcined in the same manner but were not subjected to the alcohol conditioning.

The catalyst tablets prepared above were compared to one another by using them as catalysts for the oxidation of propylene to acrolein. The reaction was conducted in a 40 cc fixed-bed reactor equipped with a suitcase heater. Product analysis was conducted in the same manner using the same equipment as in the fluid-bed catalyst examples. The contact time was approximately 2.2 seconds and a propylene/air/steam/nitrogen feed of 1/9/5/3 was used. Reactions were conducted at a temperature of approximately 349° C. The results of this comparison are reported in Table II.

TBALE II

COMPARISON OF ALCOHOL-CONDITIONED AND UNCONDITIONED FIXED-BED CATALYSTS IN THE OXIDATION OF PROPYLENE TO ACROLEIN AND ACRYLIC ACID

| Ex. | Alcohol Conditioned | Propylene Conversion (Wt %) | % Corrected PPC* to Acrolein | Acrylic Acid | Total |
|---|---|---|---|---|---|
| B.1 | No | 89.6 | 68.2 | 14.2 | 82.4 |
| B.2 | No | 90.7 | 68.6 | 14.2 | 82.8 |
| 3.1 | Yes | 90.6 | 70.1 | 13.7 | 83.8 |
| 3.2 | Yes | 91.0 | 69.9 | 14.3 | 84.2 |

$$*\% \text{ Corrected PPC} = \frac{\% \text{ PPC}}{\text{Carbon Balance}} \times 100$$

As was demonstrated with the fluid-bed catalyst, the alcohol conditioned catalyst produced a higher per pass conversion of acrolein and acrylic acid than the unconditioned catalyst.

Although the invention has been described in considerable detail through the preceding examples, these examples are for the purpose of illustration only and it is understood that variations and modifications can be made by one skilled in the art without departing from the spirit and scope of the appended claims.

What is claimed is:

1. An improved method for preparing a supported, mixed-metal oxide oxidation catalyst, the method comprising:

(1) forming a catalyst precursor with a volatile content from a support and the mixed-metal components, (2) reducing the volatile content of the precursor of (1), and (3) calcining the precursor of (2) to a finished catalyst, the improvement comprising conditioning the catalyst precursor with a solution of at least one $C_1$–$C_8$ aliphatic alcohol that is substantially free of water and is substantially removed upon calcination subsequent to reducing the volatile content of the precursor and prior to calcining the precursor to a finished catalyst.

2. The method of claim 1 where the alcohol is methanol or ethanol.

3. The method of claim 1 where the catalyst precursor is conditioned by contacting the precursor with boiling alcohol.

4. The method of claim 3 where the precursor is contacted with the boiling alcohol for at least about 5 minutes at about atmospheric pressure.

5. The method of claim 3 where the precursor is contacted with the boiling alcohol for at least about 60 minutes at about atmospheric pressure.

6. The method of claim 1, wherein the support of the mixed-metal oxide oxidation catalyst is silica or alumina.

7. The method of claim 6 where the mixed-metal oxide oxidation catalyst is of the empirical formula $$Mo_{12}P_{0-3}M_{0.01-10}O_x \quad (I)$$

where

M is at least one of potassium, rubidium, cesium, barium, zinc, cadmium, titanium, calcium, magnesium, tungsten manganese, tantalum, zirconium, cerium, nickel, cobalt, chromium, iron, thallium, bismuth, copper, vanadium, niobium, a rare earth metal, arsenic and antimony; and x is a number that satisfies the valence requirements of the other elements present.

8. The method of claim 7 where M is a combination of at least three metal components and the subscript of phosphorus is a positive number.

9. The method of claim 8 where M includes an alkali metal, bismuth and at least one of iron, cobalt and nickel.

10. The method of claim 7 where the catalyst contains bismuth.

* * * * *